(12) United States Patent
Thrush et al.

(10) Patent No.: US 9,841,378 B2
(45) Date of Patent: Dec. 12, 2017

(54) SERIES ABSORBANCE GLASS AND INTERFERENCE FILTERS

(71) Applicant: BIO-RAD LABORATORIES, INC., Hercules, CA (US)

(72) Inventors: Evan Thrush, San Anselmo, CA (US); Steve Swihart, Walnut Creek, CA (US); Neeraj Bhatt, Fremont, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 14/699,755

(22) Filed: Apr. 29, 2015

(65) Prior Publication Data

US 2015/0316479 A1    Nov. 5, 2015

Related U.S. Application Data

(60) Provisional application No. 61/987,391, filed on May 1, 2014.

(51) Int. Cl.
  *G01N 21/64* (2006.01)
(52) U.S. Cl.
  CPC ..... *G01N 21/6456* (2013.01); *G01N 21/6486* (2013.01); *G01N 2021/6439* (2013.01);
  (Continued)
(58) Field of Classification Search
  CPC .......... G01N 21/6456; G01N 21/6486; G01N 2021/6471; G01N 2021/6482;
  (Continued)

(56) References Cited

U.S. PATENT DOCUMENTS 5,050,991 A * 9/1991 Welch ............................ 356/326
5,572,369 A * 11/1996 Estelle ...................... G02B 9/16
  359/785

(Continued)

FOREIGN PATENT DOCUMENTS

WO    2005/113832 A2    12/2005

OTHER PUBLICATIONS

International Search Report and Written Opinion dated Aug. 5, 2015, from International Application No. PCT/US2015/028214 (14 pages).

(Continued)

*Primary Examiner* — David Porta
*Assistant Examiner* — Blake Riddick
(74) *Attorney, Agent, or Firm* — Kilpatrick Townsend & Stockton LLP

(57) ABSTRACT

An imaging assembly and processing system that includes a sample platform having a target region which can hold a sample, where the sample can be marked with fluorescent or phosphorescent markers. The imaging assembly can have an excitation light module proximate to the sample platform that emits light to excite the markers, and a lens module positioned to receive emission light from excited markers in target region. At least one series filter assembly or interference filter can be arranged in front of, behind, or both in front of and behind the lens module. The assembly includes a light sensor and a processor and imaging module configured to process data captured by the light sensor. Images of the sample are generated based on the emission light from the sample that transmit through and are filtered by the lens assembly and series filter assembly or interference filter.

27 Claims, 11 Drawing Sheets

(52) U.S. Cl.
CPC ............ *G01N 2021/6471* (2013.01); *G01N 2021/6482* (2013.01); *G01N 2201/062* (2013.01); *G01N 2201/0627* (2013.01); *G01N 2201/0638* (2013.01); *G01N 2201/12* (2013.01)

(58) Field of Classification Search
CPC ..... G01N 2201/062; G01N 2201/0638; G01N 2201/12; G02B 7/03; G02B 7/006; G02B 7/02; G02B 7/20; G02B 7/021; G02B 3/0075; G02B 2003/0093; G02B 21/362; G02B 21/36; G02B 27/018; G02B 27/0025; G02B 27/0037; G02B 27/0081
USPC ............................ 250/458.1, 459.1; 359/811
See application file for complete search history.

(56) References Cited

U.S. PATENT DOCUMENTS

| | | |
|---|---|---|
| 6,262,837 B1 | 7/2001 | Nagano et al. |
| 7,053,397 B1 | 5/2006 | Nishioka |
| 7,453,568 B2 | 11/2008 | Kawamata et al. |
| 7,683,310 B1 * | 3/2010 | Sinclair ................ G01S 7/4804 250/203.1 |
| 7,692,162 B2 | 4/2010 | Mehta et al. |
| 8,575,569 B2 | 11/2013 | Yajima et al. |
| 8,785,885 B1 * | 7/2014 | Jutamulia et al. ......... 250/458.1 |
| 2002/0167652 A1 * | 11/2002 | Ueyama ................ G02B 3/00 355/67 |
| 2004/0095640 A1 | 5/2004 | Weiss |
| 2004/0181344 A1 * | 9/2004 | Stephanopoulos et al. ..... 702/20 |
| 2005/0046810 A1 * | 3/2005 | Nakamura ............ G03B 21/22 353/102 |
| 2006/0166368 A1 * | 7/2006 | Berkelman .................... 436/86 |
| 2006/0203244 A1 * | 9/2006 | Nilson et al. ................. 356/417 |
| 2006/0204997 A1 * | 9/2006 | Macloszek et al. ............. 435/6 |
| 2007/0030334 A1 * | 2/2007 | Nishizawa .................... 347/245 |
| 2008/0149855 A1 * | 6/2008 | Mehta et al. ............. 250/492.1 |
| 2009/0080194 A1 | 3/2009 | Bouzid et al. |
| 2011/0008034 A1 * | 1/2011 | Kamatani ............ G02B 13/001 396/133 |
| 2011/0057117 A1 * | 3/2011 | Fawcett et al. ............ 250/458.1 |
| 2012/0045757 A1 | 2/2012 | Kjaerulff et al. |
| 2012/0105949 A1 | 5/2012 | Cummings et al. |
| 2013/0078660 A1 * | 3/2013 | Wang et al. .................... 435/15 |
| 2013/0331667 A1 * | 12/2013 | Colvin et al. ................. 600/316 |
| 2014/0055652 A1 | 2/2014 | Hasegawa et al. |
| 2014/0206580 A1 * | 7/2014 | Grudzien ........... G01N 21/6486 506/18 |
| 2014/0273194 A1 * | 9/2014 | Handique et al. ......... 435/288.7 |
| 2015/0141777 A1 * | 5/2015 | Emken et al. ................ 600/316 |

OTHER PUBLICATIONS

Extended European Search Report dated Feb. 9, 2017 in EP 15785338.3, 9 pages.

\* cited by examiner

SERIES ABSORBANCE GLASS AND INTERFERENCE FILTERS

CROSS-REFERENCE TO RELATED APPLICATIONS

This application claims priority to and the benefit of U.S. Provisional Patent Application No. 61/987,391, entitled "SERIES ABSORBANCE GLASS AND INTERFERENCE FILTERS" filed May 1, 2014, the disclosure of which is hereby incorporated by reference.

FIELD OF THE INVENTION

The present invention generally relates to the field of imaging and apparatus for imaging biological and chemical test and assay results. More specifically, many embodiments are directed to a compact and efficient imaging apparatus for viewing electrophoresis gels, nucleic acid blots, protein blots, Western blots, or similar biochemical tests and assays at using fluorescent or phosphorescent markers.

BACKGROUND OF THE INVENTION

Instruments and apparatus systems that are used for viewing, recording, and analyzing the results of biological and chemical tests and assays often require instrumentation that provide for the transmission either or both of specific wavelengths and polarization of light to sufficiently image the target. Such instrumentation can include cameras, microscopes, and the like, and can use the light emitted by fluorescent or phosphorescent markers in samples to form an images and identify characteristics of a sample, such as structure or the presence of particular components, to which the markers have attached. In such instrumentation, an image formed by the light wavelengths emitted by the markers in the sample can be reduced in quality by interference from other light sources, considered in such a context as light pollution. Light pollution that reaches an image capturing sensor of imaging instrumentation can reduce the quality and accuracy of the imaged sample.

SUMMARY OF THE INVENTION

The following presents a simplified summary of some embodiments of the invention in order to provide a basic understanding of the invention. This summary is not an extensive overview of the invention. It is not intended to identify key or critical elements of the invention or to delineate the scope of the invention. Its sole purpose is to present some embodiments of the invention in a simplified form as a prelude to the more detailed description that is presented later.

Embodiments of the present disclosure include an imaging assembly having a sample platform having a target region, an excitation light module arranged proximate to the sample platform, a lens module arranged to receive light emitted from the target region, a first series filter assembly, positioned along an optical path in line with the lens module, where the first series filter assembly is constructed of an absorbance glass having at least one side coated with a thin film interference filter layer, a light sensor arranged to receive light emitted from the lens module, and an imaging module configured to process data captured by the light sensor. In aspects of such embodiments, the first series filter assembly can be positioned in front of the lens module along the optical path or behind the lens module along the optical path. In other aspects, the imaging assembly can include a second series filter assembly, positioned along an optical path in line with the lens module, where the second series filter assembly is constructed of an absorbance glass having at least one side coated with a thin film interference filter layer, where the first series filter assembly can be positioned in front of the lens module along the optical path and where the second series filter assembly can be positioned behind the lens module along the optical path. In some embodiments, a first series filter assembly can be positioned with the interference filter side proximate to the sample platform, while in alternative embodiments, a first series filter assembly can positioned with the absorbance glass side proximate to the sample platform. In some aspects, the excitation light module can include an excitation light array that can emit more than one wavelength of light. In yet further aspects, the imaging assembly excitation light module can be arranged in an epi-illumination configuration. In further aspects, the lens module can include one or more lenses arranged as an optical baffle. In some aspects, the imaging assembly can include baffles proximate to the front of the lens module. In other aspects, the sample platform can be configured to support a Western blot sample in the target region. In some aspects, the imaging assembly absorbance glass can be a borosilicate glass.

Further embodiments of the present disclosure can include an imaging system having a processor configured to control at least an excitation light module and an imaging module, a sample platform having a target region arranged proximate to the excitation light module, a lens module arranged to receive light emitted from the target region, a first series filter assembly, positioned along an optical path in line with the lens module, where the first series filter assembly can be constructed of an absorbance glass having at least one side coated with a thin film interference filter layer, and a light sensor arranged to receive light emitted from the lens module, electronically coupled to the imaging module, where the imaging module can be configured to process data captured by the light sensor. In aspects, the imaging system processor further includes a non-transitory computer readable media, having computer program instructions to control operation of the excitation light module. In further aspects, the imaging system processor further includes a non-transitory computer readable media having computer program instructions to control the imaging module and generate an image based on light emitted from the target region that transmits through the lens module. In some aspects, the imaging system can further include a display module electronically coupled to the light sensor and processor, configured to display the generated image based on light emitted from the target region that transmits through the lens module. In other aspects, the imaging assembly absorbance glass can be a borosilicate glass.

In alternative embodiments of the present disclosure, an imaging assembly can include a sample platform having a target region, an excitation light module arranged proximate to the sample platform, a lens module arranged to receive light emitted from the target region, a first interference filter, positioned along an optical path in line with and in front of the lens module, a second interference filter, positioned along an optical path in line with and behind the lens module, a light sensor arranged to receive light emitted from the lens module, and an imaging module configured to process data captured by the light sensor. In some aspects, the imaging assembly according excitation light module further includes an excitation light array that can emit more than one wavelength of light. In other aspects, the imaging assembly lens module includes one or more lenses arranged as an optical baffle.

BRIEF DESCRIPTION OF THE DRAWINGS

Illustrative aspects are described in detail below with reference to the following drawing figures.

DETAILED DESCRIPTION OF THE INVENTION

Figure 1:
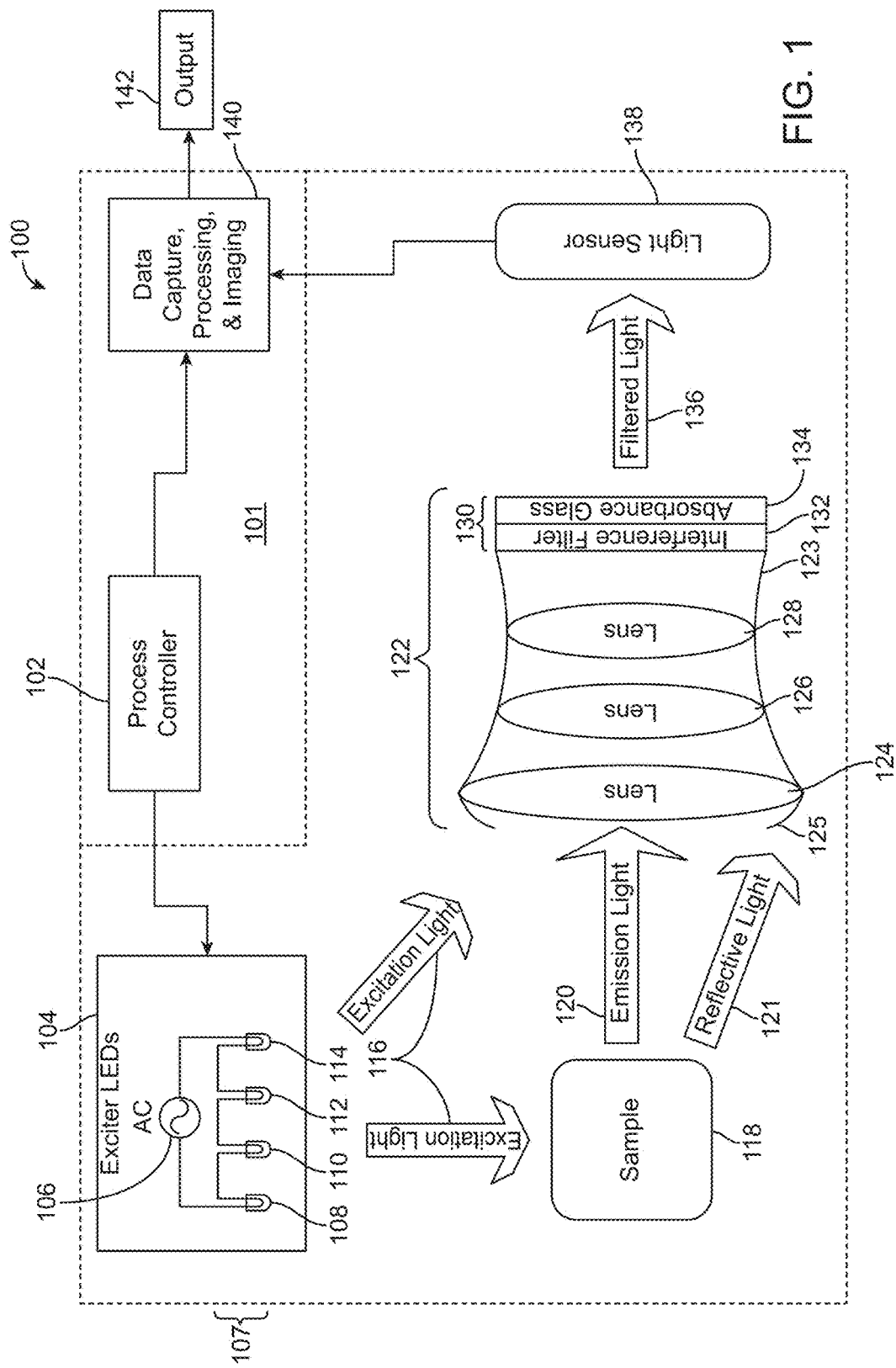
FIG. 1 is a schematic representing elements of an imaging system exciting a sample and filtering reflective light from the sample through a filtering module to an image sensor, according to some aspects or embodiments.

Throughout this description for the purposes of explanation, numerous specific details are set forth in order to provide a thorough understanding of the many embodiments disclosed herein. It will be apparent, however, to one skilled in the art that the many embodiments may be practiced without some of these specific details. In other instances, well-known structures and devices are shown in diagram or schematic form to avoid obscuring the underlying principles of the described embodiments.

Imaging systems, apparatus, and instrumentation for imaging results from various biological, chemical, and/or biochemical tests and assays often use the light emitted by fluorescent or phosphorescent markers in samples to form an images and identify characteristics of a sample. As used herein, a "marker" can refer to an amino acid, nucleic acid, or similar biological structure corresponding to a DNA or RNA sequence, an antigen, other protein, or other biological structure of interest that has been labeled with a detectable molecule that re-emits light upon excitation by an excitation light source. Such markers may be a specifically constructed probe-and-label structure inserted into a sample environment, while in some aspects a marker can be a native protein with naturally occurring fluorescent or phosphorescent structures. In embodiments of the present disclosure, such markers are designed and constructed to chemically bond with a desired biological or chemical structure in a sample, and to also carry a fluorophore which can be part of a chemical structure referred to as a fluorescent member. A fluorophore can re-emit light upon light excitation, i.e. fluoresce, and in embodiments may emit light upon excitation by light of a specific wavelength. In further alternative embodiments, such markers can carry a phosphor which can be part of a chemical structure referred to as a phosphorescent member, and may re-emit light upon light excitation, i.e. phosphoresce. In yet further alternative embodiments, Raman spectroscopy techniques may be used to excite molecules and thereby measure vibrational, rotational, and other low-frequency modes in a protein structure. In aspects, the fluorescent member can continuously emit light if excited, and an image of a sample can be observed based on the markers that bind to parts of the sample once any unbound markers have been removed from the sample. In other aspects, the fluorescent member can emit light only when bound to a specific biological structure, allowing for an image of a biological sample to be observed based on the light emission of the bound markers. Sensors in imaging instrumentation observing the emitted light, in communication with data processing components, can generate images based on the emitted light and thereby identify characteristics of a sample, such as a structure of the sample, or the presence of particular biological or chemical materials, based on the construction of the markers.

The intensity of light from a fluorescent member, however, may be equal to or less than the intensity of light surrounding the imaging instrumentation. The light sensors of the instrumentation may pick up such ambient background light, or light pollution, such that images of sample based on fluorescent emissions are reduced in accuracy, clarity, and overall quality. In some aspects, the light simply reflecting off of parts of the instrumentation or parts of the sample can be light pollution sources. Similarly, the original excitation light used to cause the fluorophores to fluoresce may be captured by the light sensors, distorting the image of the sample of interest. Light pollution from reflective light can be observed, in particular, with Western blots, as the sample observed in a Western blot is often a highly reflective white blot. The fact that the blot is white means that it is very effective at scattering excitation light, regardless of wavelength. Thus, there can be an excess of reflected excitation light directed toward a lens assembly and light sensor. The excessive reflective light, is effectively noise and can wash out the desired signal from the fluorescence light emission from the markers and sample An approach to reduce the amount of light pollution is to construct structural aspects of imaging instrumentation to minimize the entry of ambient background light or light pollution, but such construction can reduce the usability of the instrumentation. In such constructed structures, there is a desire to view the entirety of a sample, but imaging apparatuses can be limited in size due to the strength and intensity of the emission light. In other words, the fluorescence may be limited, thus the lenses and imaging sensors capturing the light must remain relatively close to the sample illuminated. Thus, wide angle observation of a sample can be useful to capture a complete image of a sample. However, structures that can help in reducing the amount of reflected and excess excitation light coming in from the corners of an apparatus may also disadvantageously block the desired emissive light from the corners, edge, perimeter, or circumference of a sample, not adequately capturing the emission light. The difference between capturing desired emission light while obstructing undesired light pollution can be within a narrow wavelength or intensity range, making the construction of such an imaging apparatus relatively complicated.

As described in aspect and embodiments, absorbance materials and interference filters can control the amount, angles, polarization, and wavelengths of light that reach a light sensor in imaging instrumentation. Similarly, the construction and arrangement of lenses can also control the amount, angles, polarization, and wavelengths of light that may reach a light sensor (alternatively referred to as a photosensor) in imaging instrumentation. The use of absorbance materials and interference filters can thus reduce the amount of undesired light pollution captured by the imaging apparatus without unduly reducing the desired signal of fluorescent or phosphorescent emission light captured from an excited sample.

As used herein, the terms "off-normal light" and "high angular light" generally refer to light incident on a surface that is not directly perpendicular or normal to the plane of that surface. In aspects, the surfaces receiving light can be a single lens, the first lens of a lens barrel, an interference filter, an absorbance glass, or a series filter. In some aspects, "off-normal light" and "high angular light" can refer specifically to light incident on a surface at least about 25° to about 30° divergent from the normal axis of light, or in other words, at least about 25° to about 30° away from the perpendicular axis to the plane of the first lens of a lens barrel, an interference filter, an absorbance glass, or an assembly of such elements in series.

As used herein, unless otherwise indicated, relative positional terms including, but not limited to, "before", "after", "in front of", "behind", and the like refer to the positioning of elements relative to the optical path of light incident on or transmitting through such elements. As discussed herein, such elements positioned relative to each other are optical structures, can include lenses, filters, absorbance glass, light sensors, and the like.

Thin film interference filters can have blocking characteristics, reflecting one or more spectral bands or lines and transmits others, while maintaining a nearly zero coefficient of absorption for all wavelengths of interest. Interference filters are known for filtering as used in fluorescence imagers. A limitation of interference filters, however, is their angular performance—as the angle of incident light increases, the wavelength passed by the filter shifts to shorter wavelengths toward (i.e. blue shift) the excitation light. The result is that with standard fluorescence imagers, a higher background or a glow exists at the edges of the captured image, which is progressively worse with increasing radius from image center. A further limitation can be that reflected or scattered excitation light occurring at a high angle of incidence on an interference filter can be transmitted through the interference filter due to the blue shift of the filter, which will result in light pollution at the plane of the a photosensor behind the interference filter, and thereby reduce sensitivity.

As incident light diverges from normal, an interference filter will pass shorter and shorter wavelengths of light, which can result in the transmission of undesired light transmitted through the perimeter region of the filter. Such transmission can result in imaging with excess light sensed along the perimeter of an image, also referred to as a halo. In embodiments, the transition of light along an optical path can pass through high index of refraction materials and low index of refraction materials which reduce the transmission of some wavelengths of light at high angular incidences. With interference filters made by successively depositing layers of materials of high and low incidence of refraction, as the wavelength of incident light increases, the sensitivity of a dielectric filter to the angle of incident light increases due to the smaller effective refractive index at wavelengths corresponding to red light versus wavelengths corresponding to blue light. Accordingly, increasing the effective refractive index of a film layer stack greatly reduces the angular dependence of interference filters. In some aspects, using ultra-high index materials in such an interference filter can reduce transmission of light at high angular incidences more significantly. Moreover, a more robust angular performance can reduce the amount of diffusely scattered light in the system from being transmitted through an interference filter.

In aspects, filters that block transmission of light over specific ranges of wavelength ($\lambda$, measured in nanometers), can reduce the amount of halo effect light captured in an image, particularly with blots and gels designed to image in the near infrared (NIR) spectrum ($\lambda$ from about 800 nm to 2,500 nm). However, the use of interference filters alone can result in images with light pollution artifacts or shifting. For example, an interference filter for wavelengths of light with $\lambda$ in a range of about 820 nm to 860 nm, which in some aspects can be at about 830 nm, can result in an image with sufficient halo effect and/or background light pollution that reduces the accuracy of the image. Similarly, an interference filter for wavelengths of light with $\lambda$ in a range of about 700 nm to 740 nm, which in some aspects can be at about 730 nm, can result in light pollution, such as an image exhibiting shift of the transmitted light toward narrower wavelengths, in particular around an excitation wavelength of about 670 nm. In further embodiments, an interference filter can be configured to pass wavelengths bands of light with $\lambda$ in a range of about 300 nm to about 1,000 nm.

Absorbance glass, on the other hand, is a light filter having a coefficient of absorption that reduces the overall transmission of light through the absorbance glass, and can be measured in terms of optical density ("OD"). Generally, in fluorescence imagers that use absorbance glass as an absorbance filter, the level of blocking of the absorbance filter is insufficient to block all of the excitation light that may transmit through a sample, reflect off of a sample or sample platform.

In embodiments, absorbance glass can reduce the amount of light from off-normal that passes through to the sensor. Light that enters absorbance glass from a high angle has a longer optical path through the absorbance glass for light to pass and transmit through. Absorbance glass, however, can also "autofluoresce", which refers to the behavior of the absorbance glass, where due to the color of the absorbance glass, the absorbance glass can absorb some of the excitation light and (depending on the color and wavelength of excitation light) re-emit that light, similar to the fluorescent action of markers a sample. Accordingly, in some embodiments, the dielectric interference filter side of the series filter can be positioned facing the sample, reducing the amount of color-based autofluorescing of the absorbance glass. In some embodiments, the absorbance glass can be a borosilicate glass, as borosilicate glass generally exhibits less autofluorescing characteristics than other glasses used for absorbance glasses.

In embodiments of the present disclosure, an interference filter and absorbance glass arranged in series within an imaging apparatus operate to reduce the amount of background light or light pollution that would otherwise reach an imaging sensor. The combination of an interference filter and absorbance glass arranged in series, referred to herein as a "series filter assembly", provides for a greater transmission ratio of the desired signal relative to background light. The signal to background ratio of emission light from a fluorophore is greater with a series filter assembly than is obtained with either an interference filter or absorbance glass alone. In some embodiments, relative to an incident optical path, an interference filter is arranged first, in front of an absorbance glass filter positioned subsequently in the optical path of the targeted signal light. In other embodiments, relative to an incident optical path, the absorbance glass filter is arranged first, in front of the interference filter positioned subsequently in the optical path of the targeted signal light. In embodiments, the interference filter and absorbance glass arranged in series can particularly reduce the amount of undesired light transmitted along the perimeter of an imaging apparatus and image sensor, and any scattered light generated by blocking high-incidence light, thereby improving accuracy and resolution along the edges of an image formed by the transmitted light. Such a series filter assembly can further improve the accuracy and resolution of in the center of, and across the entirety of, an image formed by the transmitted light. Since the filtering capability of an absorbance filter is proportional to path length in a filter at a given wavelength, incident light rays having a higher angle (away from normal) blocked by the filter will be blocked more efficiently than rays closer to perpendicular (normal) incidence. Aspects of the interference filter and absorbance glass arranged in series can particularly reduce the amount background light in the near infrared (NIR) spectrum.

In embodiments, one or more or series filter assemblies, can be coupled with a lens module, positioned along an optical path of incident light to be aligned in front of, behind, or both in front of and behind the lens module. In such embodiments, relative to the optical path of incident light, the one or more series filter assembly and lens module are arranged to have the same normal axis; in other words, in line with each other providing a straight optical path for incident light. In some embodiments, lenses toward the front the lens module are larger in diameter than lenses toward the back of the lens module; in such embodiments, a series interference filter positioned behind the lens module can be relatively less expensive than a comparable series interference filter positioned in front of the lens module.

In embodiments, performance of an imaging system can also be improved by placing interference filters both in front of a lens module and behind the lens module. An interference filter behind a lens can be positioned between the lens and a charge coupled device (CCD). Mechanical requirements can include a configuration having two filter wheels, arranged in proximity to the lens. Embodiments using such a dual filter configuration can significantly reduce background noise below a level of background reduction that can be achieved with a single interference filter alone, either in front of or behind a lens.

While the many embodiments disclosed herein are generally directed to an efficient imaging apparatus for imaging fluorescent samples or markers with excitation lighting, the imaging apparatus described herein can be used for any application where lighting and imaging of phosphorescent, chemiluminescent, or bioluminescent samples or markers can be performed with potential light pollution from an excitation light source or other lighting source, where similar or analogous lens and filter structures would be appropriate or advantageous. Aspects of the present disclosure can include the imaging apparatus being arranged as an epi-illumination system or as a trans-illumination system.

FIG. 1 is a schematic representing elements of an imaging system exciting a sample and filtering reflective light from the sample through a filtering module to an image sensor 100. A process controller 102, which can be microprocessor and other circuitry with an input-output interface for executing programming instructions held within a non-transitory computer readable medium 101, controls an excitation light module 104. The excitation light module can include an excitation light power source 106 which can direct electrical current to one or more light sources or lighting elements. In some aspects, the excitation light module 104 includes light sources emitting different wavelengths of light. In some aspects, the light sources or lighting elements are light emitting diodes (LEDs), while in other aspects the light sources can be colored light bulbs, or structures forming an excitation light array. The excitation light module 104 can include a deep red light LED 108, a red light LED 110, a green light LED 112, and a blue light LED 114. The collection of light sources or lighting elements can be referred to as an excitation light array 107. In some embodiments, the deep red light LED 108 can emit infrared light (IR), including NIR light, while in other embodiments, there can be a separate light source for an IR channel. The process controller 102 can control the excitation light module 104 to activate the light sources individually, sequentially, simultaneously, or in combinations and variations thereof. In some aspects, each light source can be activated individually to precisely control the wavelength of excitation light 116 emitted by the excitation light module 104. In some applications, the excitation light 116 emitted by the excitation light module 104 is a sequential powering of the individual light sources.

The excitation light 116 can illuminate a sample 118, a lens module 122, and any other structures within the sample region of an imaging system proximate to the light sources. The excitation light array 107 located in the excitation light module 104 is particularly proximate to the sample platform which can support and hold a sample 118. The sample 118 can be particularly positioned in a target region of the imaging apparatus, configured to receive excitation light from the excitation light module 104 and to emit emission light. In some embodiments, the excitation light array 107 and light sources can be about 20 mm distant, about 30 mm distant, about 40 mm distant, or about 70 mm distant from the sample 118 to be illuminated. The sample 118 can be a gel or a blot, such as a Western blot or a gel documentation application that contains chemical elements such as markers or stains, which can be fluorescent markers or phosphorescent markers. Markers in the sample 118 can react when excited by the excitation light 116, for example, a fluorescent marker can fluoresce when excited by excitation light 116 of a specific wavelength. In aspects, some markers in a sample 118 will react to light wavelengths emitting from a deep red light LED 108, a red light LED 110, a green light LED 112, a blue light LED 114, light sources or lighting elements emitting equivalent wavelengths of light, or combinations thereof. These specific light sources are provided and configured to emit wavelengths of light that specifically excite particular fluorophores and markers that can be in a sample. The fluorescing of a fluorescent marker in a sample 118, or light emissions from other markers, is emission light 120 which can be indicative of characteristics or qualities of the sample 118 as held within a gel or blot. The excitation light 116 can also simply reflect off of the sample 118 and structures proximate to the sample 118, generating reflective light 121 that is not indicative of the characteristics or qualities of the sample 118 or marker in a sample 118.

The lens module 122 can comprise a lens barrel 123 that act as walls to define a space in which one or more lenses can be arranged and oriented. In the embodiment shown, the lens module 122 includes a first lens 124, a second lens 126, and a third lens 128. In alternative embodiments, the lens module 122 can include one lens, two lenses, or four or more lenses. The emission light 120 emitting from the markers in the sample 118 is in part directed toward and captured by the lens module 122, entering the lens barrel 123. The amount of excitation light 116 and reflective light 121 that enters the lens module 122 can be reduced by baffles 125 at the front of the lens module 122. Reduction of light that that is not indicative of the characteristics or qualities of the sample 118 such as excitation light 116 and reflective light 121 helps to improve the quality of the signal of the emission light 120 that enters the lens module 122.

In embodiments, the lens barrel 123 can include baffles 125, which can be physical extensions of the lens barrel 123 walls that obstruct high angle light from entering the lens module 122. The baffles 125 can be proximate to the perimeter of the first lens 124, at least in part covering the first lens 124 and thereby preventing entry of light from high angles off-normal into the first lens.

In embodiments, the light that enters the lens module 122 is primarily emission light 120 with a minimized amount of excitation light 116 of reflective light 121 entering the lens module 122. In the embodiment illustrated, the light that enters the lens module 122 is focused sequentially through the first lens 124, the second lens 126, and third lens 128, where the first lens 124 is proximate to the sample 118. In some embodiments, the first lens 124 can have a diameter greater than either or both of a diameter of the second lens 126 and a diameter of the third lens 128. In some embodiments, the second lens 126 can have a diameter greater than either or both of a diameter of the first lens 124 and a diameter of the third lens 128. In alternative embodiments, the third lens 128 can have a diameter greater than either or both of a diameter of the first lens 124 and a diameter of the second lens 126. Further, in some embodiments, the first lens 124 can have a thickness greater than either or both of a thickness of the second lens 126 and a thickness the third lens 128. In some embodiments, the second lens 126 can have a thickness greater than either or both of a thickness of the first lens 124 and a thickness of the third lens 128. In alternative embodiments, the third lens 128 can have a diameter greater than either or both of a diameter of the first lens 124 and a diameter of the second lens 126.

In some aspects, shape of the lens module 122 itself can further function as an optical baffle. As illustrated in FIG. 1, the lenses in the lens module 122 decrease in diameter along the optical path of the emission light 120, specifically, the first lens 124 has a larger diameter than the second lens 126, which in turn has a larger diameter than the third lens 128. Incident light entering the lens module 122 from a high angle, passing through a particular lens arrangement as illustrated, can be directed toward the interior walls of the lens barrel 123. Accordingly, the configuration of lenses in the lens barrel 122 can function to reduce the amount of off-normal light that passes through the entirety of the lens module 122.

The lens module 122 can include a series filter assembly 130 coupled to the lens barrel 123, distal from the sample 118. The series filter assembly 130 can include paired or layered interference filter 132 coupled with absorbance glass 134. In some embodiments, the series filter assembly 130 can be an interference filter 132 mechanically coupled to an absorbance glass 134, but where the optical surfaces of the interference filter 132 and absorbance glass 134 are not in direct contact. In an embodiment as illustrated, the interference filter 132 side of the series filter assembly 130 is arranged proximate to the third lens 128. In other embodiments, the absorbance glass 134 side of the series filter assembly 130 can be arranged proximate to the third lens 128. After emission light 120 has passed through lenses in the lens module 122, the emission light 120 interfaces with and is filtered by the series filter assembly 130. The emission light 120, focused by the lenses of the lens module 122, is generally perpendicular to the surface of the series filter assembly 130 when the emission light 120 interfaces with the side of the series filter assembly 130 proximate to the sample 118. In some embodiments, the one or more lenses in the lens module 122 can be arranged and configured to direct off-normal light that does enter the lens module 122 toward the interior surface of the lens barrel 123; in other words, any off-normal light can be refracted toward the interior walls of the lens module 122 and does not transmit through the entirety of the lens module 122.

In an exemplary embodiment, the series filter assembly 130 can be configured to have excitation filter, emission filters, and LED light sources as set forth in Table 1:

TABLE 1

| Channel | LED Wavelength | Excitation Filter | Emission Filter | Spectral Separation | Color Glass |
|---|---|---|---|---|---|
| Blue | 477 nm | 475/30 | 532/28 | 28 | No |
| Green | 520 nm | 525/30 | 602/50 | 37 | No |
| Red | 620 nm | 625/30 | 697/55 | 29.5 | Yes - 660 nm |
| Deep Red | 660 nm | 664/27 | 730/40 | 32.5 | Yes - 695 nm |
| IR | 770 nm | 774/24 | 845/40 | 32.5 | Yes - 800 nm |

In the exemplary embodiment set forth in Table 1, the filter nomenclature indicates the center wavelength of the filter followed by the full width of the filter range at half the maximum transmission of the peak wavelength. The spectral separation value is an indication of the spectral distance between the red side of the excitation filter and the blue side of the emission filter. Larger spectral separation can be better as less parasitic excitation light will be transmitted through the emission filter and create less background pollution.

Some of the light sources can further be coupled with a colored glass, which can further filter light toward a given wavelength.

In embodiments, the interference filter 132 can have a thickness of about one to about five millimeters (1-5 mm). In some embodiments, the interference filter 132 can be a layer of dielectric materials with various refractive indices. In some embodiments, the interference filter 132 can have a plurality of thin film dielectric layers applied on a substrate, where the dielectric layers can be alternating layers of two or more dielectrics. The thickness of each dielectric layer can be proportional to the wavelength of light emitted by a sample. For example, each thin film layer can have a thickness of $\lambda/4$ or $\lambda/2$ relative to the wavelength $\lambda$ of the light incident on the interference filter. The thickness of the thin film dielectric layers can be further modified to account for the index of refraction of the material of the dielectric layer. Dielectric materials that can be used for interference filters can have an index of refraction from about 1.0 to about 2.5. Further, interference filters 132 as used herein can have an optical density of about OD4 to about OD6.

In embodiments, the absorbance glass 134 can have an optical density of about OD2 to about OD5. An interference filter 132, or a combined interference filter 132 and absorbance glass 134, having an OD6 can reduce transmission of light through the absorbance glass 134 to 0.0001% of the original incident light luminance. In other embodiments, the absorbance glass 134 can be constructed from more than one panes of absorbance glass having specific optical densities coupled in series with each other. For example, in such embodiments, a pair of absorbance glass panes each having an optical density of about OD3 can be coupled to form an absorbance glass 134 having about OD6 as utilized in a series filter assembly 130.

The interface between the interference filter 132 and the absorbance glass 136 can be configured to have a minimal difference between their indexes of refraction. In some embodiments, the interference filter 132 and the absorbance glass 136 can be bonded together by an external frame, such as by the walls of the lens barrel 123. In other embodiments, the series filter assembly 130 can be held in a separate structure, for example a filter wheel, and held proximate to the end of a lens barrel 123 distal from a sample. In some embodiments, the interference filter 132 can be one or more film layers deposited, such as by sputter deposition or chemical vapor deposition, onto the absorbance glass 136, thereby coating the absorbance glass 136 with at least one layer of an interference filter 132 film. In further embodiments, the interference filter 132 and absorbance glass 136 can be laminated together to form the series filter assembly 130. In yet further embodiments, the interference filter 132 and absorbance glass 136 can be physically coupled together to form and operate as a series filter assembly 130 but not expressly bonded to each other; for example, where both the interference filter 132 and absorbance glass 136 are snugly fit in a pocket of a filter wheel. In some aspects, the absorbance glass can be a borosilicate glass.

The emission light 120 that transmits through and emits from the series filter assembly 130 is filtered light 136. The filtered light 136 can be of a wavelength and intensity that is representative of the emission light 120 from the sample. The filtered light 136 that emits from the lens module 122 is more accurately representative of the markers excited on the sample 118 than the light present before the lens module 122, which includes excess excitation light 116 and reflective light 121. The filtered light 136 that transmits through and emits from the series filter assembly 130 is incident on a light sensor 138. In some aspects, the light sensor 138 can be a photosensor, charge coupled device (CCD), or the like. The light sensor 138 can receive the filtered light 136, and determine characteristics of the filtered light 136 including the wavelength, the intensity, and the like.

The light sensor 138 transmits data regarding the filtered light 136 to a data capture, processing, and imaging (DCPI) module 140 (alternatively referred to as an imaging module). The DCPI module can be electronically and informationally coupled to the process controller 102. In aspects, the DCPI module 140 can receive data capture, processing, and imaging instructions from the process controller 102, transmitted via the non-transitory computer readable medium 101 according to either or both of user input and computer program instructions. The DCPI module 140 can organize data received from the light sensor 138, providing digital images representative of the sample 118 to an output 142. In aspects, the output 142 can be a separate non-transitory computer readable medium such as a database or a computer processing system. In some aspects, the output 142 can be a display configured to show on a screen or other such display apparatus the digital image generated by the DCPI module 140 based on the information sensed by the light sensor 138.

Figure 2:
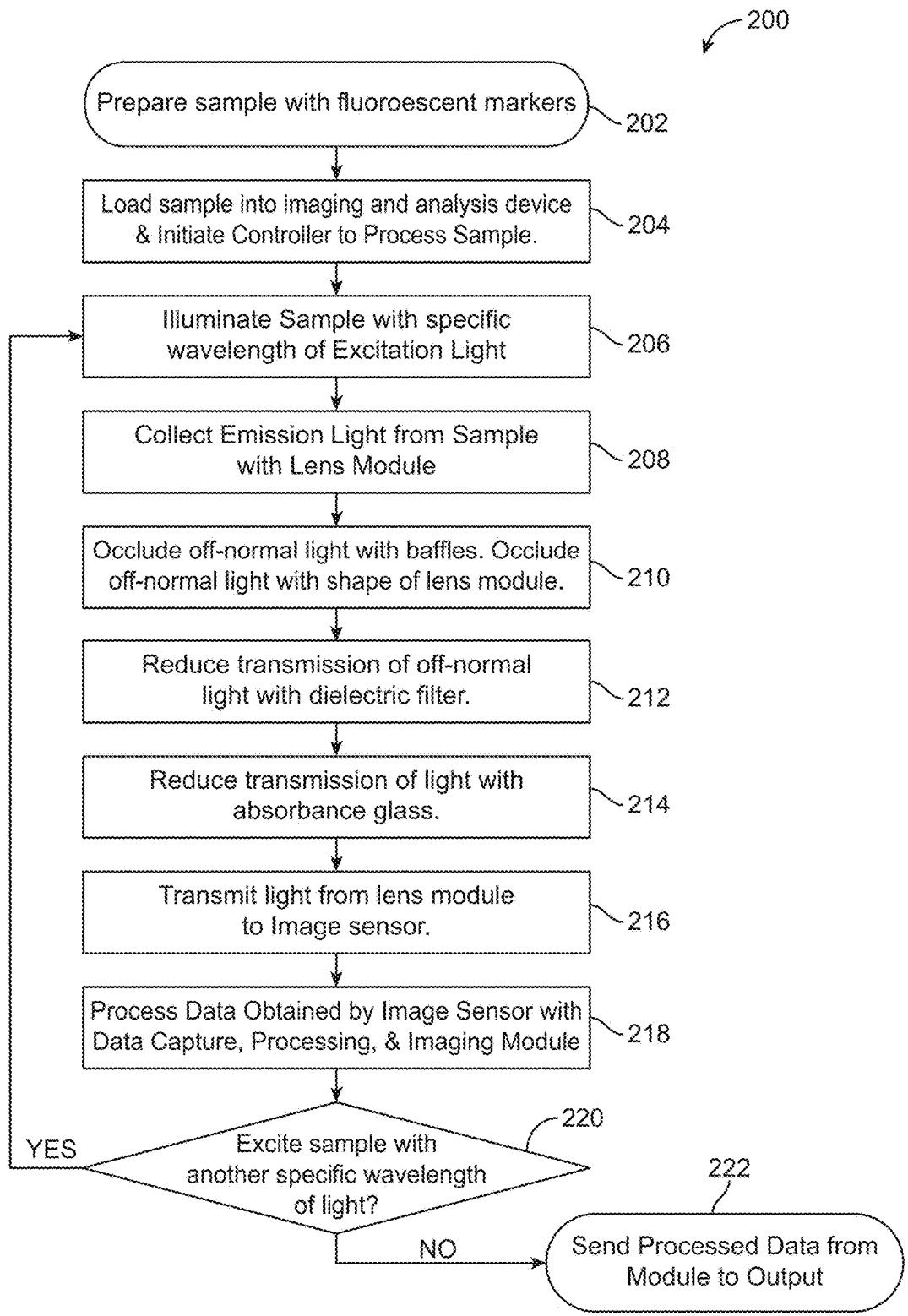
FIG. 2 is a flowchart illustrating an exemplary method and process for preparing a sample with luminescent members and processing luminosity data from the sample, according to some aspects or embodiments.

In some embodiments, a method of preparing, processing, and acquiring data from a sample is disclosed. FIG. 2 is a flowchart illustrating an exemplary method and process for preparing a sample with luminescent members and processing luminosity data from the sample 200. At a first step 202, a sample can be prepared with fluorescent markers. In some aspects, the sample can be prepared with luminescent markers including, but not limited to, fluorescent markers and phosphorescent markers. At step 204, the sample can be loaded into an imaging and analysis device. A controller can initiate the processing of the sample, where the controller can be responsive to either or both of user input and computer program instructions. The controller can transmit process instructions to the imaging and analysis device according to parameters including: one or more wavelengths of light with which to illuminate a sample, one or more light sources with which to illuminate a sample, durations of time to illuminate a sample with a given light source, and intensity of a light source used to illuminate a sample. Such parameters are exemplary and not an exhaustive collection of instructions that the controller can transmit to the imaging and analysis device.

At step 206, the sample can be illuminated with a specific wavelength of light, emitted by at least one excitation light source. In some aspects, only one excitation light source will be illuminated at any one time. In alternative aspects, two or more excitation lights can be illuminated concurrently or sequentially. In some aspects, when a sample may have more than one marker responsive to different wavelengths of light, the controller can run iterations of illumination, returning to step 206 for each iteration that requires a distinct wavelength of light for illumination.

At step 208, emission light from the sample, the light from markers that is emitted due to excitation from the light source(s), is collected with a lens module, and transmitted through the lens module. At step 210, which is in effect concurrent with step 208, off-normal light, such as the original excitation light, reflective light reflecting from the surface, or reflective light reflecting from the structure of the sample itself, is occluded from entering the lens module. In some aspects, structural baffles obstruct off-normal light from entering the lens module. In other aspects, the construction, arrangement, and shape of the one or more lenses in the lens module direct off-normal light that does enter the lens module toward the interior walls of the lens module. In embodiments, a series filter assembly is located within the lens module behind the one or more lenses, which are relatively distal from the emission light source, and can include an interference filter coupled to absorbance glass.

At step 212, the emission light from the sample that has passed through the lenses in the lens module interfaces with an interference filter, which in some aspects can be a dielectric filter, and in other aspects can be a dichroic filter. The interference filter allows only light of specific wavelengths to pass through the filter. In some aspects, the interference filter can allow only light of a specific polarity to pass through the filter.

At step 214, light that passes through the interference filter interfaces with absorbance glass. The absorbance glass can generally reduce the overall transmission of light through the absorbance glass. In some aspects, the absorbance glass can be configured to absorb light in specific wavelength ranges, thereby reducing transmission of light in those wavelength ranges.

In alternative embodiments, the lens module is constructed such that emission light interfaces with the absorbance glass before the interference filter. In other words, along the optical path of the emission light the absorbance glass is proximate to the emission light source and the interference filter is relatively distal from the emission light source.

In further alternative embodiments, the series filter assembly can be located before the at least one lens in the lens module, or in other words, is relatively proximate to the emission light source.

At step 216, light that passes through the series filter assembly is transmitted from the lens module to an image sensor. The image sensor can measure and capture the filtered emission light and relay data representative of the filtered emission light to a DCPI module.

At step 218, a DCPI module receives imaging data from the image sensor and processes the imaging data. The processed imaging data can be a digital image identifying illumination from markers that have been excited in a sample.

At step 220, a decision query is made, whether the sample is to be illuminated with another wavelength of excitation light. In some aspects, a single sample can be illuminated with at least two light sources having different wavelengths of light and exciting at least one different phosphorescent or fluorescent marker in the sample. If the decision query result is positive, the process returns to step 206 and continues the process, illuminating the sample with a wavelength of light different than a wavelength of light already used to excite the sample. If the decision query result is negative, the process continues to step 222, ultimately concluding the process. In some aspects, the decision query result is obtained from either or both of user input and a computer program instruction set, relayed by the controller.

At step 222, imaging data that has been processed by the DCPI is sent to an output module. In some aspects, imaging data of a sample obtained from excitation light at a first wavelength can be processed and output while the imaging system and apparatus continues to image the sample at one or more different second wavelengths. In some embodiments, the output can be to a non-transitory computer readable medium such as a database. In other embodiments, the output can be a visual display screen. In further embodiments, the processed data can be sent to multiple output receivers.

Figure 3A:
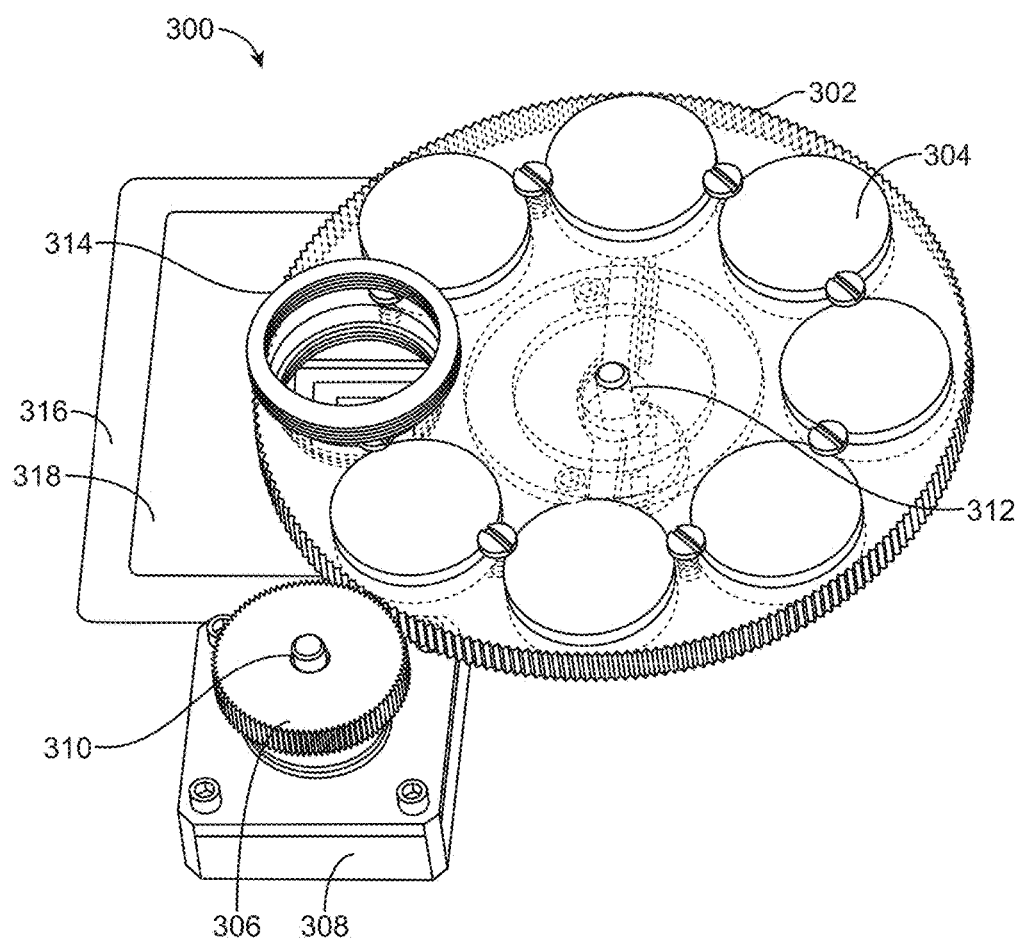
FIG. 3A is a rear isometric illustration of a filter wheel and mounting structure that can be utilized as a component of an imaging system and apparatus, according to some aspects or embodiments.

FIG. 3A is a rear isometric illustration of a filter wheel and mounting structure 300 that can be utilized as a component of an imaging system and apparatus. The filter wheel 302 can be configured to secure and hold at least one filter 304 proximate to the perimeter of the filter wheel. In embodiments as illustrated, the filter wheel 302 can hold multiple filters 304 held equidistantly along the perimeter of the filter wheel, in slots or pockets configured to securely mount such filters 304. In alternative embodiments, there can be more than one filter 304 arranged asymmetrically within the filter wheel, and at locations relatively proximate or distal from the perimeter of the filter wheel 302. In embodiments, the filter wheel 302 can have a circumference surface that is notched or toothed and coupled to an operative gear 306, such that when the operative gear 306 rotates, driven by a gear motor 308 and mounted to a gear axis 310, the filter wheel 302 is correspondingly rotated. The filter wheel 302 can be mounted to a filter wheel axis 312, and is arranged such that the at least one filter 304 mounted within the filter wheel 302 aligns with a lens mount 314. The lens mount 314 is located within a lens module casing 316, which in some embodiments can include a casing backing 318. When the operative gear 306 drives the filter wheel 302 to rotate, the individual filter 304 located over the lens mount 314 region is changed. In embodiments, the at least one filters 304 can be interference filters coupled with absorbance glass in series. In aspects where multiple filters 304 are present in a filter wheel 302, each filter 304 can have combinations of interference filters and absorbance glasses distinct from the other filters 304 in the filter wheel 302.

Figure 3B:
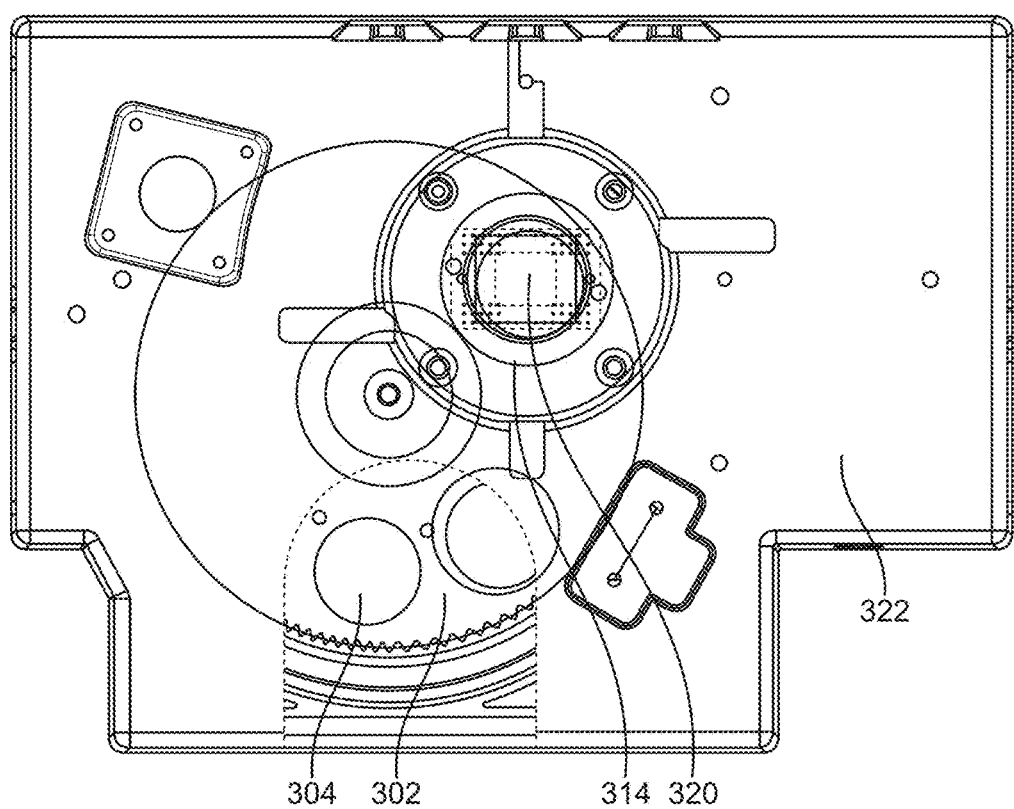
FIG. 3B is a front profile illustration of a filter wheel and mounting structure within a casing, according to some aspects or embodiments.

FIG. 3B is a front profile illustration of a filter wheel 302 and mounting structure within a casing. In some embodiments as illustrated, the filter wheel 302 is partially exposed and partially covered by a casing front 322. The casing front 322 includes an aperture through which light can be transmitted and interface with an image sensor 320. The area in which the image sensor 320 is located can be bounded by the perimeter of the lens mount 314, the lens mount being coupled to the casing. In some embodiments, the lens mount 314 holds one or more lenses that focus light incident through the casing front aperture onto the image sensor 320. The filter wheel 302 can be arranged between the lens mount 314 and the image sensor 320 and thereby position a filter 304 between the lens mount 314 and the image sensor 320. The filter 304 can reduce the transmission of light incident at undesired wavelengths or angles. In alternative embodiments, the filter wheel 302 can be completely covered by the casing front 322, except for the aperture that allows light to reach the image sensor 320.

Figure 3C:
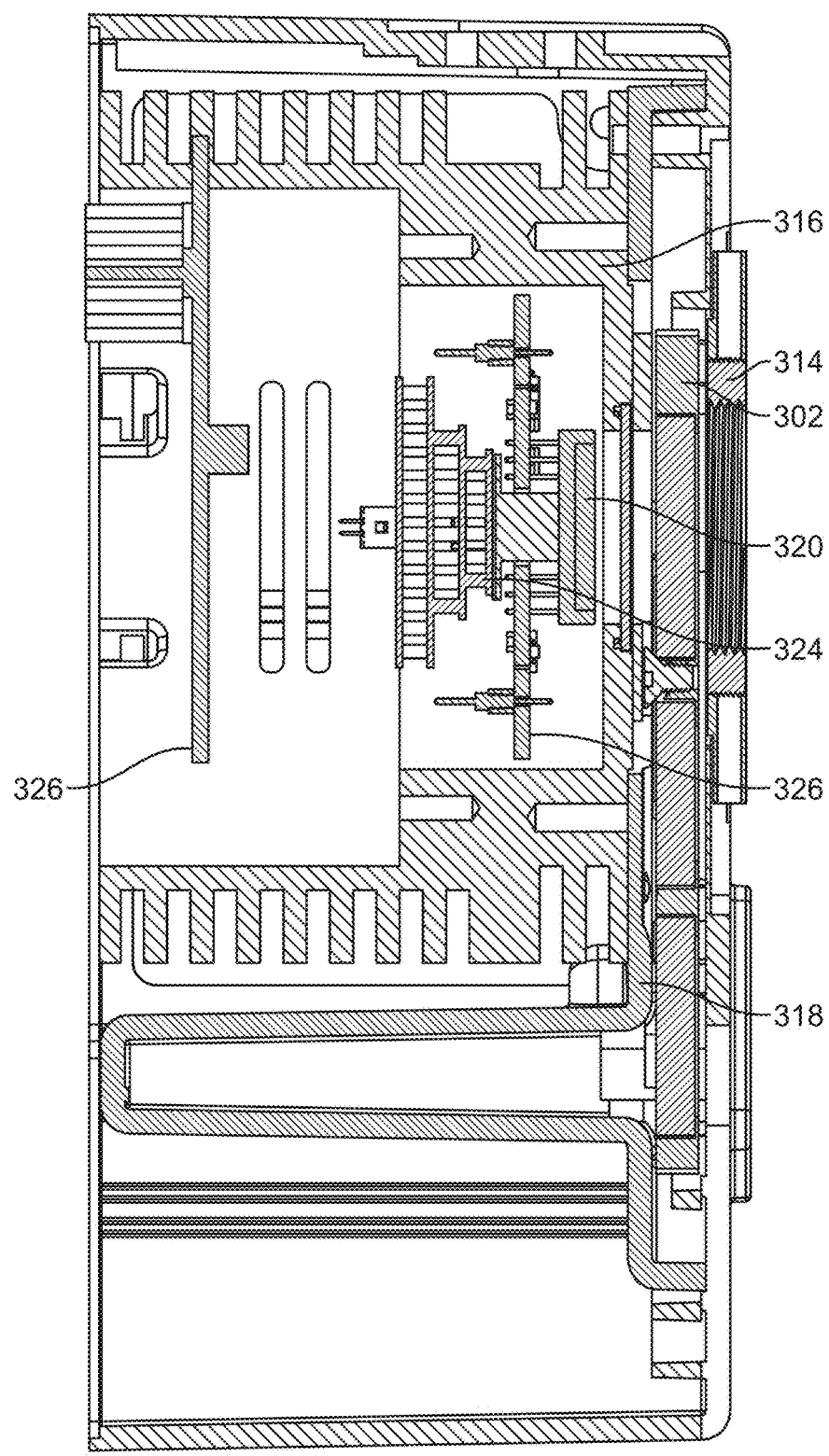
FIG. 3C is a side cross-sectional illustration of the filter wheel mounting structure and casing, according to some aspects or embodiments.

FIG. 3C is a side cross-sectional illustration of the filter wheel mounting structure and casing. Light along an optical path incident on the mounting structure and casing can enter the lens module casing 316 through the aperture defined by the lens mount 314. Light that passes through the aperture defined by the lens mount 314 can interface with and transmit through one or more filters held by a filter wheel 302 located behind the lens mount 314. The casing backing 318 can be arranged further behind the filter wheel 302, and can further position and secure the image sensor 320, or an aperture for an optical path incident onto the image sensor 320. The image sensor can be coupled to a cooling element 324. The image sensor 320 can be further connected to processing circuitry 326 that can relay data from the image sensor 320 to subsequent processing modules or other non-transitory computer readable media.

Figure 4A:
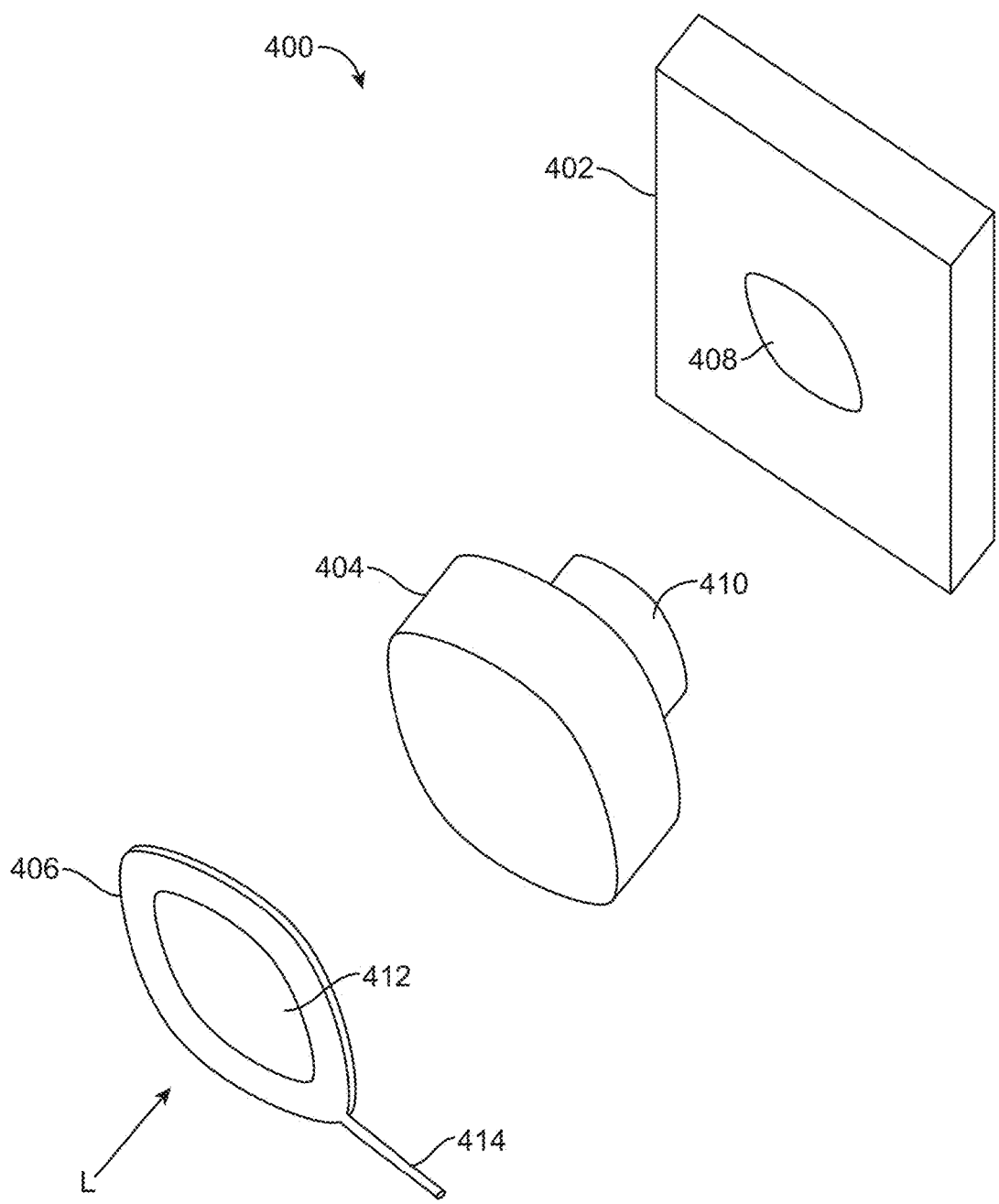
FIG. 4A is an exploded schematic illustration of a filter positioned in front of a lens module and camera module, according to some aspects or embodiments.

FIG. 4A is an exploded schematic illustration of a filter positioned in front of a lens module and camera module 400.

In embodiments, a camera module 402 can house an imaging sensor and circuitry for relaying, processing, or otherwise manipulating image data captured by the image sensor. A lens module 404 can be coupled to the camera module 402, where the lens module 404 can have a lens mounting segment 410 that can mechanically couple with and secure to a lens receiving mount 408 in the camera module 402. In embodiments as illustrated, a filter 406 can be positioned in front of the lens module 404. The filter 406 can position a filter element 412 along the optical path of incident light L before the lens module 404, and in some embodiments can be set into position by a filter arm 414. In aspects, the filter element 412 can be an interference filter, absorbance glass, or an interference filter and absorbance glass coupled in series. In alternative embodiments, a filter wheel can hold and position at least one filter element 412 along the optical path of incident light L before the lens module 404, where rotation of the filter wheel can position separate or different filter elements 412 before the lens module. In such embodiments as illustrated, the filter element 412 can reduce the amount of off-normal incident light L before entering and being focused by the lens module. Similarly, the filter element 412 can reduce the amount of incident light L at particular wavelengths before entering and being focused by the lens module.

Figure 4B:
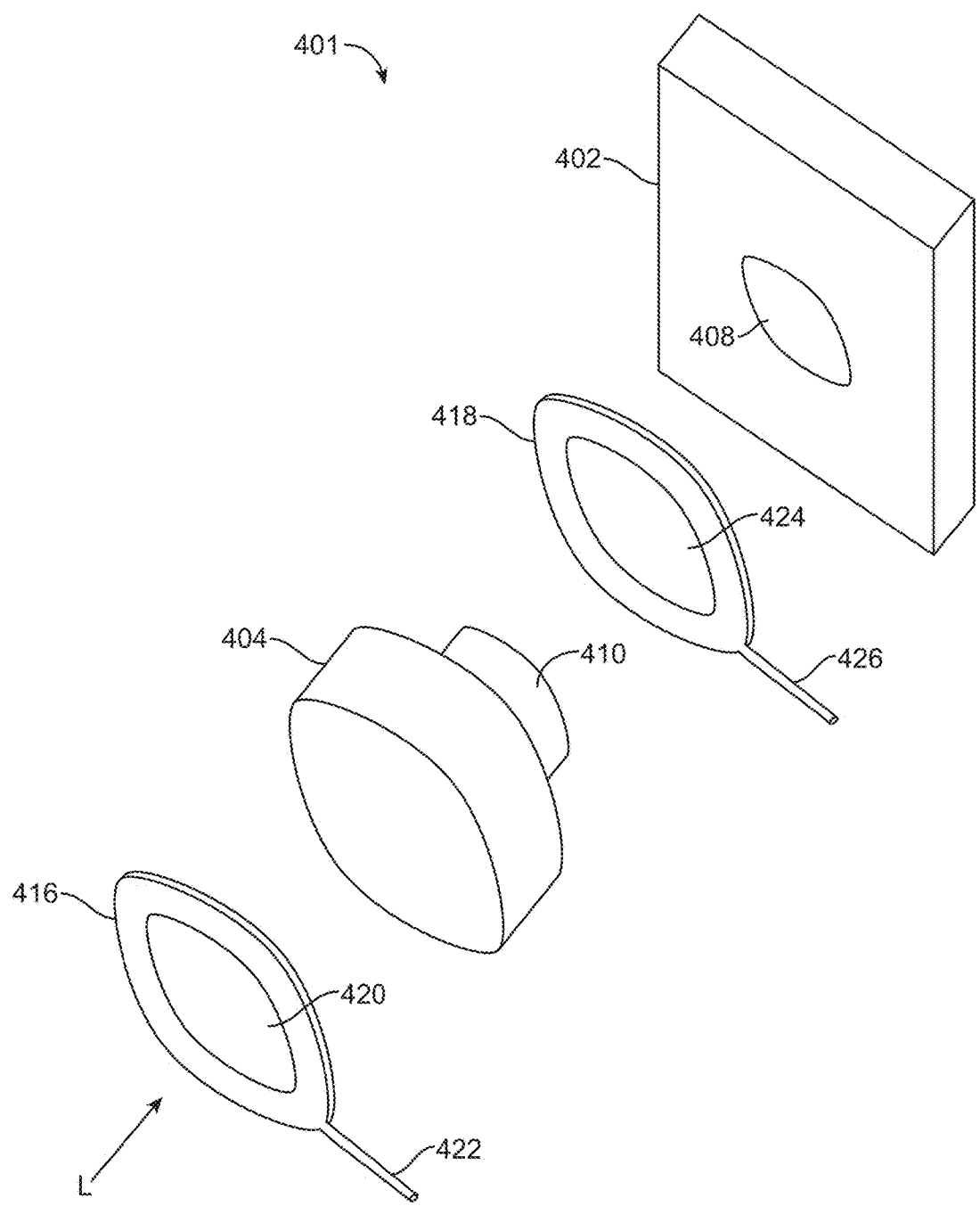
FIG. 4B is an exploded schematic illustration of a lens module and camera module with a first filter positioned in front of the lens module, and with a second filter positioned behind the lens module and before the camera module, according to some aspects or embodiments.

FIG. 4B is an exploded schematic illustration of a lens module and camera module with a first filter positioned in front of the lens module, with a second filter positioned behind the lens module and before the camera module 401. In embodiments, the camera module 402 can house an imaging sensor and circuitry for relaying, processing, or otherwise manipulating image data captured by the image sensor. The lens module 404 can be coupled to the camera module 402, where the lens module 404 can have a lens mounting segment 410 that can mechanically couple with and secure to a lens receiving mount 408 in the camera module 402. In embodiments as illustrated, a first filter 416 can be positioned in front of the lens module 404. The first filter 416 can position a first filter element 420 along the optical path of incident light L before the lens module 404, and in some embodiments can be set into position by a first filter arm 422. Further, a second filter 418 can be positioned behind the lens module 404. The second filter 418 can position a second filter element 424 along the optical path of incident light L after the lens module 404, and in some embodiments can be set into position by a second filter arm 426. In aspects, either or both of the first filter element 420 and second filter element 424 can be an interference filter, absorbance glass, or an interference filter and absorbance glass coupled in series. In alternative embodiments, a filter wheel can hold and position at least one first filter element 420 along the optical path of incident light L before the lens module 404, where rotation of the filter wheel can position separate or different first filter elements 420 before the lens module. In similar alternative embodiments, a filter wheel can hold and position at least one second filter element 424 along the optical path of incident light L after the lens module 404, where rotation of the filter wheel can position separate or different second filter elements 424 after the lens module and before the camera module 402. In such embodiments as illustrated, either or both of the first filter element 420 and second filter element 424 can reduce the amount of off-normal incident light L before entering and being focused by the lens module. Similarly, either or both of the first filter element 420 and second filter element 424 can reduce the amount of incident light L at particular wavelengths before entering and being focused by the lens module. In some embodiments, the first filter element 420 and the second filter element 424 can be made of the same elements, or can be identical, passing incident light L of the same wavelength or angular orientation. In some embodiments, the first filter element 420 and the second filter element 424 can be made of different elements, passing incident light L of different wavelengths and angular orientations.

In other embodiments, both of the first filter element 420 and second filter element 424 can be positioned along the optical path of incident light L before the lens module 404. In embodiments where both of the first filter element 420 and second filter element 424 are positioned along the optical path of incident light L before the lens module 404, either the first filter element 420 or the second filter element 420 can be relatively closer to the lens module 404. In yet further embodiments, both of the first filter element 420 and second filter element 424 can be positioned along the optical path of incident light L after the lens module 404. In embodiments where both of the first filter element 420 and second filter element 424 are positioned along the optical path of incident light L after the lens module 404, either the first filter element 420 or the second filter element 420 can be relatively closer to the lens module 404

Figure 5A:
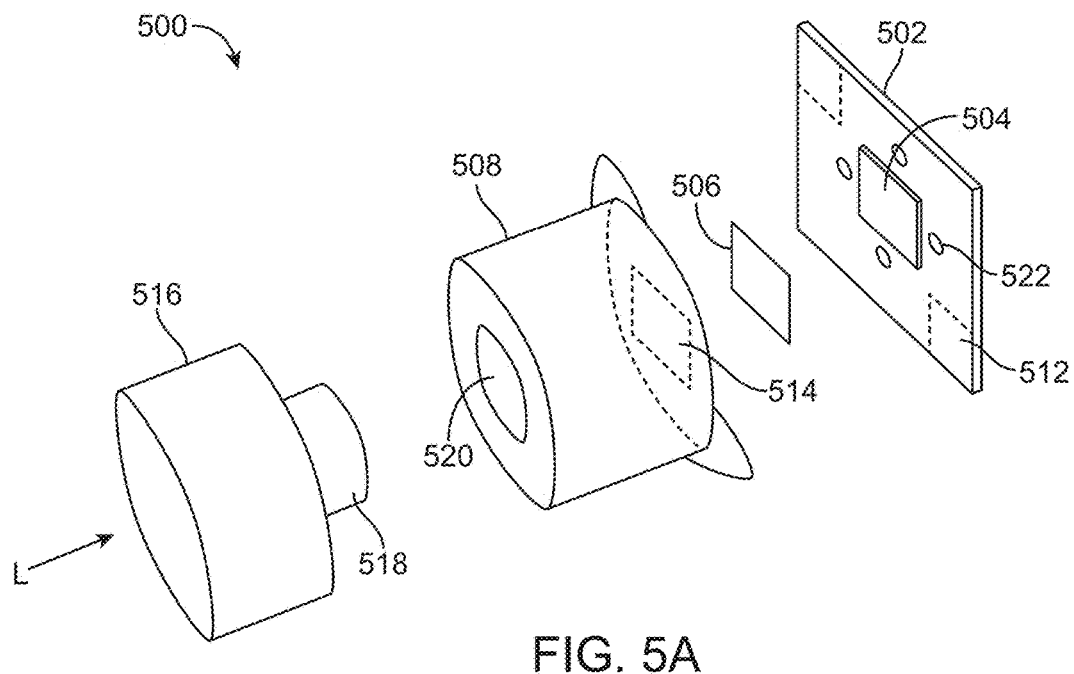
FIG. 5A is an isometric exploded schematic illustration of a filter positioned behind a lens module and camera module, according to some aspects or embodiments.

FIG. 5A is an isometric exploded schematic illustration of a filter positioned behind a lens module and camera module 500. In embodiments, a camera board 502 (which can be a printed circuit board) provides a mounting location for an image sensor 504. In some embodiments, the image sensor 504 can be positioned proximate to the center of the camera board 502. A filter element 506 can be positioned before the image sensor 504, filtering incident light L before it reaches the image sensor 504. In aspects, the filter element 506 can be an interference filter, absorbance glass, or an interference filter and absorbance glass coupled in series. A support module 508 can function as a lens mount, and can be positioned to cover and secure the filter element 506 and image sensor 504 within a support module filter cavity 514. In embodiments, the support module 508 can include one or more support module flanges 510 that can be mechanically coupled to the camera board, and in aspects mechanically coupled to camera board mounting sections 512. The support module 508 can be additionally or alternatively mounted to the camera board 502 proximate to the image sensor 504. In such embodiments, support module receiving holes 522 can be located around the image sensor 504 on the camera board 502, and mechanically couple with elements of the support module 508, which can further align the support module filter cavity 514 over the image sensor 504 and filter element 506. In embodiments, a lens module 516 is positioned in front of the filter element 506 and image sensor 504. The lens module 516 can include a lens module mounting segment 518 configured to mechanically couple with a support module lens cavity 520. In the embodiment as illustrated, with a filter element 506 arranged behind the lens module 516, the location of the filter element 506 can further increase the amount of high angle light, refracting through the lens module 516, blocked from transmitting through the filter element 506.

Figure 5B:
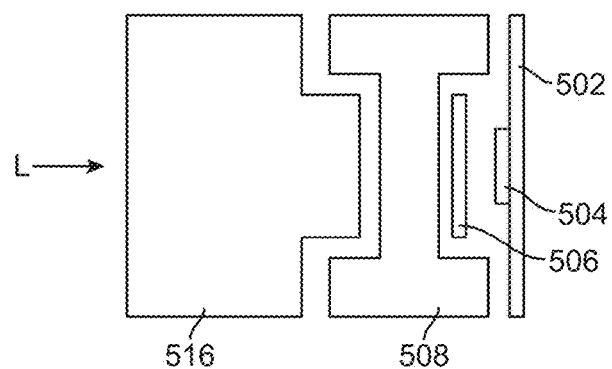
FIG. 5B is an exploded side profile schematic of a filter positioned behind a lens module and camera module, according to some aspects or embodiments.

FIG. 5B is an exploded side profile schematic of a filter positioned behind a lens module and camera module 500. As illustrated, incident light L can enter the lens module 516, where one or more lenses within the lens module 516 can focus the incident light L, and in some embodiments reduce the amount of off-normal light that passes through the lens module 516. The lens module 516 can be aligned and mounted via the support module 508, the lens module 516 mechanically coupling to a receiving section of the support module 508. The lens module 508 can be partially mechanically coupled to a camera board 502, where in some embodiments the perimeter portions of the support module 508 are bonded, secured, or otherwise affixed to a surface of the camera board 502. The support module 508 can further have a cavity section, such that between the support module 508 and camera board 502, an image sensor 504 and filter element 506 can be encased. In embodiments, the image sensor 504 is mechanically bonded, secured, or otherwise affixed to the camera board 502. Further, the image sensor 504 is electronically coupled to circuitry on the camera board 502, which provides for transmission of imaging data captured by the image sensor 504 through the camera board 502 to further non-transitory computer readable media. The filter element 506 can be secured between the image sensor 504 and the support module 508 by friction between the two elements or by being otherwise affixed to either or all of the support module 508, image sensor 504, and camera board 502, and aligned over the image sensor 504 accordingly to filter incident light L that transmits through the lens module 516 onto the image sensor 504.

Figure 6:
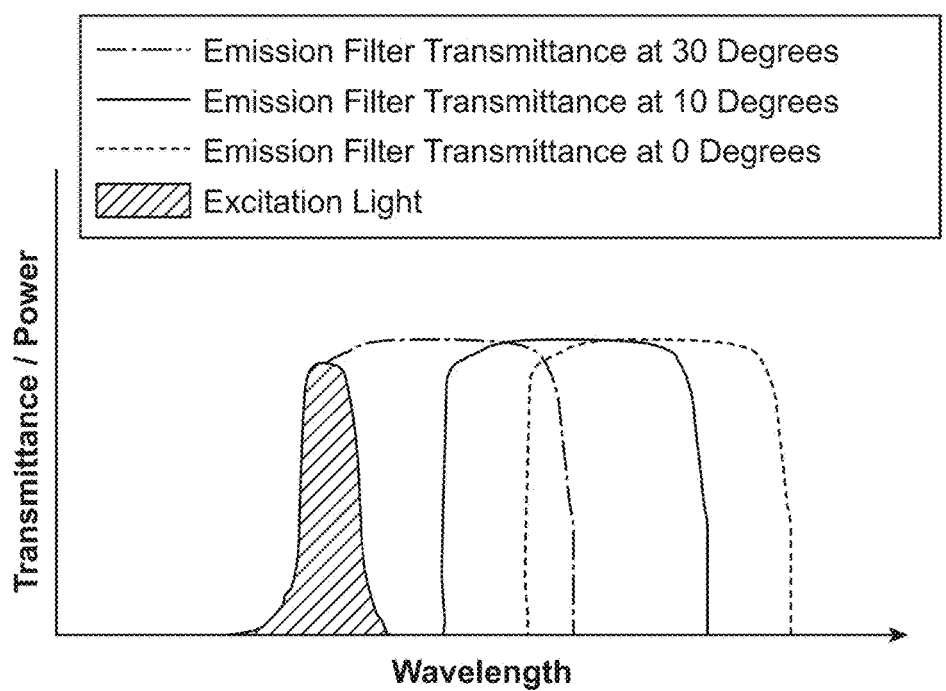
FIG. 6 is a graphical representation of blue shift that can occur to light transmitted through an interference filter as light incident on the filter surface has increasing angle divergent from the normal axis to the filter surface plane, according to some aspects or embodiments.

FIG. 6 is a graphical representation of blue shift that can occur to light transmitted through an interference filter as light incident on the filter surface has increasing angle divergent from the normal axis to the filter surface plane. As represented, an excitation light at a given excitation wavelength and excitation power can cause phosphorescent or fluorescent markers in a sample to emit emission light. In embodiments, the transmittance of emission light can be proportional to the power of the excitation light. The average wavelength of the emission light that passes through an interference filter, however, is shorter based upon the degree that the incident light deviates from normal. As represented, the emission light that is incident at 0° relative to the plane of the interference filter surface (perpendicular or normal to the filter) transmits through an interference filter having an average wavelength that is not substantively shifted from the actual wavelength of the emission light, and is most representative of the phosphorescent or fluorescent markers in a sample that are triggered by the excitation light. The emission light that is incident at 10° relative to the plane of the interference filter surface (10° in any direction deviating from the normal axis of the surface) transmits through an interference filter having an average wavelength that is shifted away from the emission light (blue-shifted) and toward the excitation light. The emission light that is incident at 30° relative to the plane of the interference filter surface (30° in any direction deviating from the normal axis of the surface, or in other words, off-normal) transmits through an interference filter having an average wavelength that is blue-shifted to a narrower range relative to the actual wavelength of the emission light, and is relatively more blue-shifted than emission light that is incident at 10° relative to the plane of the interference filter surface. The shifting allows the excitation light to pass as illustrated at 30°, which can cause light pollution on the image sensor. Such wavelength shifting of high angular light that passes through a filter can be more pronounced with light in the red, deep red, and NIR wavelength ranges, because the effective refractive index in the red wavelength ranges is typically smaller, which causes a relatively greater wavelength shift as a function of angle.

Figure 7A:
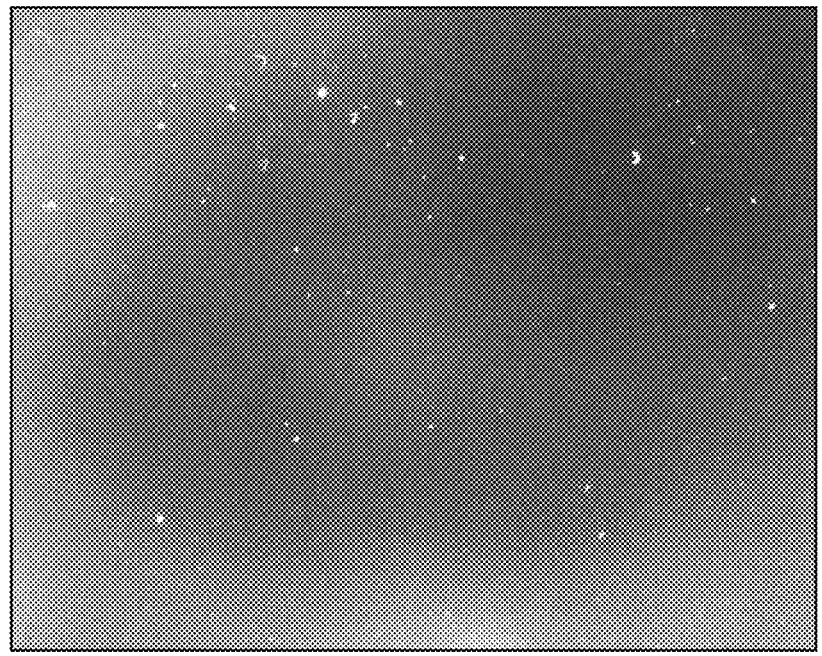
FIG. 7A is an image of emission light transmitted from a sample through a lens module having a dielectric interference filter positioned behind the lens module, without any absorbance glass, according to some aspects or embodiments.
Figure 7B:
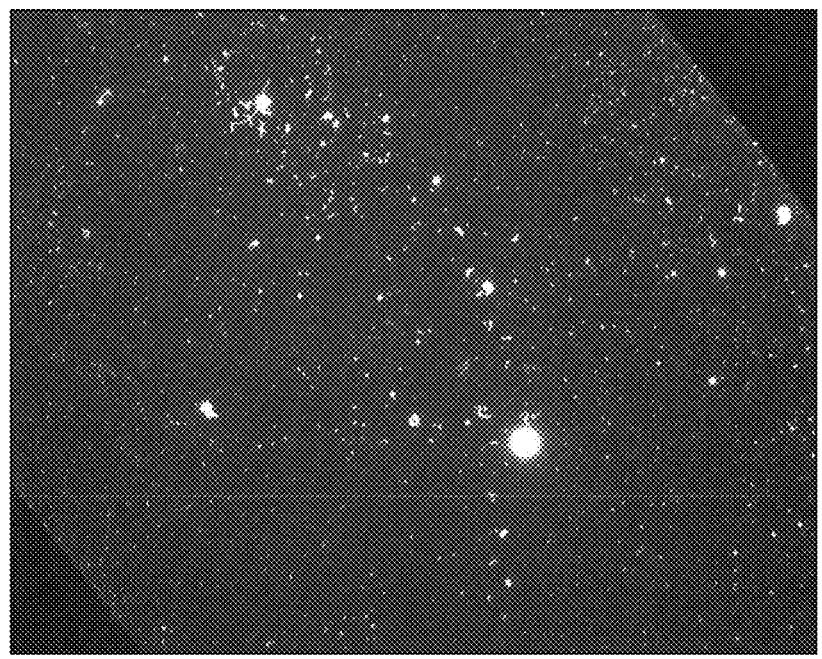
FIG. 7B is an image of light transmitted from a sample through a lens module having a dielectric interference filter and absorbance glass structure positioned behind the lens module, according to some aspects or embodiments.

FIG. 7A is an image of emission light transmitted from a sample through a lens module having a dielectric interference filter positioned behind the lens module, without any absorbance glass. FIG. 7B is an image of light transmitted from a sample through a lens module having a dielectric interference filter and absorbance glass structure positioned behind the lens module. In comparing FIG. 7A and FIG. 7B, the image captured as FIG. 7A is relatively washed out and has a noticeable halo, where the halo is representative of increased light received captured around the edges and perimeter of the image. In contrast, FIG. 7B shows relatively more distinct points of light transmission, which are more defined, and does not exhibit a halo effect.

Figure 8A:
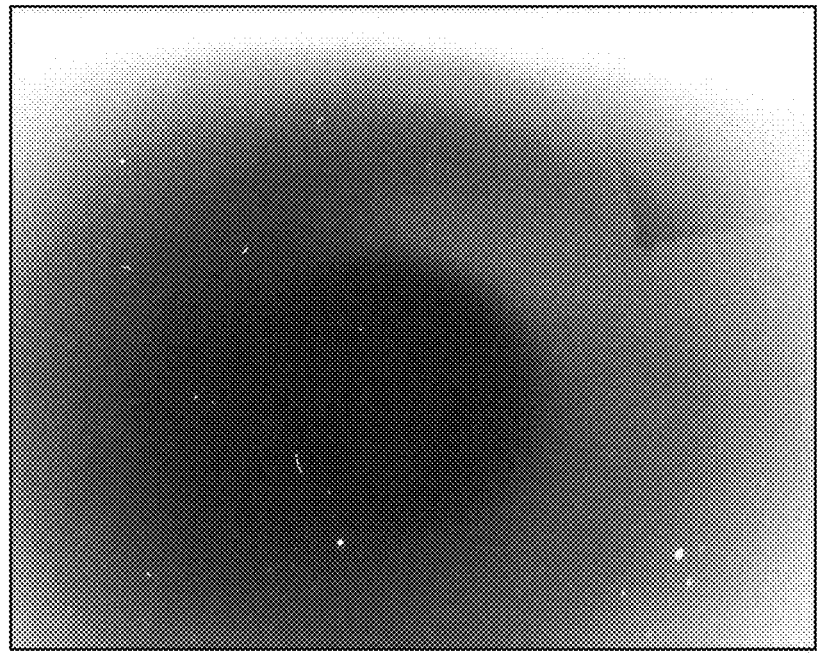
FIG. 8A is an image of light transmitted from a sample through a lens module having a dielectric interference filter positioned behind the lens module, according to some aspects or embodiments.
Figure 8B:
FIG. 8B is an image of light transmitted from a sample through a lens module having dielectric interference filters positioned both in front of and behind the lens module, according to some aspects or embodiments.

FIG. 8A is an image of light transmitted from a sample through a lens module having a dielectric interference filter positioned behind the lens module. FIG. 8B is an image of light transmitted from a sample through a lens module having dielectric interference filters positioned both in front of and behind the lens module. In comparing FIG. 8A and FIG. 8B, the image captured as FIG. 8A is relatively washed out and has a noticeable halo. In contrast, FIG. 8B shows relatively more distinct points of light transmission, which are more defined, and does not exhibit a halo effect.

As provided herein, the imaging instrumentation which captures images of samples located in a target region can be electronically coupled with an imaging instrumentation interface. Such an imaging instrumentation system and imaging instrumentation interface, can be electrically coupled to a microprocessor, (or other such non-transitory computer readable mediums) by wires or by wireless means, and thereby send imaging data signals to the microprocessor. The coupled microprocessor can collect imaging data from the imaging apparatus and/or imaging instrumentation interface can further relay collected information to other non-transitory computer readable mediums, and/or run calculations on collected data and relay the calculated result to a user-operable and/or user-readable display. The imaging data captured by the imaging apparatus can be evaluated according to computer program instructions controlling the microprocessor (either through hardware or software) to analyze or base calculations on specific wavelengths of light emitted by a sample gel, blot, or membrane, and/or specific wavelengths of light used to illuminate a sample gel, blot, or membrane.

The imaging instrumentation can include a microprocessor can further be a component of a processing device that controls operation of the imaging instrumentation. The processing device can be communicatively coupled to a non-volatile memory device via a bus. The non-volatile memory device may include any type of memory device that retains stored information when powered off. Non-limiting examples of the memory device include electrically erasable programmable read-only memory ("ROM"), flash memory, or any other type of non-volatile memory. In some aspects, at least some of the memory device can include a non-transitory medium or memory device from which the processing device can read instructions. A non-transitory computer-readable medium can include electronic, optical, magnetic, or other storage devices capable of providing the processing device with computer-readable instructions or other program code. Non-limiting examples of a non-transitory computer-readable medium include (but are not limited to) magnetic disk(s), memory chip(s), ROM, random-access memory ("RAM"), an ASIC, a configured processor, optical storage, and/or any other medium from which a computer processor can read instructions. The instructions may include processor-specific instructions generated by a compiler and/or an interpreter from code written in any suitable computer-programming language, including, for example, C, C++, C#, Java, Python, Perl, JavaScript, etc.

The above description is illustrative and is not restrictive, and as it will become apparent to those skilled in the art upon review of the disclosure, that the present invention may be embodied in other specific forms without departing from the essential characteristics thereof For example, any of the aspects described above may be combined into one or several different configurations, each having a subset of aspects. Further, throughout the foregoing description, for the purposes of explanation, numerous specific details were set forth in order to provide a thorough understanding of the invention. It will be apparent, however, to persons skilled in the art that these embodiments may be practiced without some of these specific details. These other embodiments are intended to be included within the spirit and scope of the present invention. Accordingly, the scope of the invention should, therefore, be determined not with reference to the above description, but instead should be determined with reference to the following and pending claims along with their full scope of legal equivalents.

What is claimed is:

1. An imaging assembly comprising:
   a sample platform having a target region;
   an excitation light module arranged proximate to the sample platform;
   a lens module arranged to receive light emitted from the target region, wherein the lens module includes two or more lenses arranged in an uninterrupted series as an optical baffle within a lens barrel, wherein the lenses in the lens module decrease in diameter along the optical path of the emission light and are configured to refract off-normal light toward interior walls of the lens barrel;
   a first series filter assembly, positioned along an optical path in line with the lens module, positioned in front of the lens module along the optical path, the first series filter assembly being comprised of an absorbance glass having at least one side coated with a multi-band thin film interference filter layer;
   a light sensor arranged to receive light emitted from the lens module; and
   an imaging module configured to process data captured by the light sensor.

2. An imaging assembly according to claim 1, wherein the lenses in the lens module are bi-convex lenses and decrease in diameter along the optical path of the emission light.

3. An imaging assembly according to claim 1, wherein the interference filter has an optical density of from OD4 to OD6.

4. An imaging assembly according to claim 1, further comprising a second series filter assembly, positioned along the optical path in line with the lens module, the second series filter assembly being comprised of an absorbance glass having at least one side coated with a thin film interference filter layer, wherein the absorbance glass has an optical density of from OD2 to OD5; wherein the second series filter assembly is positioned behind the lens module along the optical path.

5. An imaging assembly according to claim 1, wherein the first series filter assembly is positioned with the interference filter side proximate to the sample platform.

6. An imaging assembly according to claim 1, wherein the first series filter assembly is positioned with the absorbance glass side proximate to the sample platform.

7. An imaging assembly according to claim 1, wherein the excitation light module further comprises an excitation light array that can emit more than one wavelength of light.

8. An imaging assembly according to claim 1, further comprising structural baffles, proximate to the front of the lens module, provided in combination with the optical baffle.

9. An imaging assembly according to claim 1, wherein the sample platform is configured to support a Western blot sample in the target region.

10. An imaging assembly according to claim 1, wherein the excitation light module is arranged in an epi-illumination configuration.

11. An imaging assembly according to claim 1, wherein the absorbance glass is a borosilicate glass.

12. An imaging system comprising:
    a processor configured to control at least an excitation light module and an imaging module;
    a sample platform having a target region arranged proximate to the excitation light module;
    a lens module arranged to receive light emitted from the target region, wherein the lens module includes three or more lenses arranged in an uninterrupted series as an optical baffle within a lens barrel, further wherein the lenses in the lens module are bi-convex lenses, decrease in diameter along the optical path of the emission light, and are configured to refract off-normal light toward interior walls of the lens barrel;
    a first series filter assembly, positioned along an optical path in line with the lens module, the first series filter assembly being comprised of an absorbance glass having at least one side coated with a multi-band thin film interference filter layer; and
    a light sensor arranged to receive light emitted from the lens module, electronically coupled to the imaging module, the imaging module being configured to process data captured by the light sensor.

13. An imaging system according to claim 12, wherein the processor further comprises a non-transitory computer readable media having computer program instructions to control operation of the excitation light module.

14. An imaging system according to claim 13, further comprising a display module electronically coupled to the light sensor and the processor, configured to display a generated image based on light emitted from the target region that transmits through the lens module.

15. An imaging system according to claim 12, wherein the processor further comprises a non-transitory computer readable media having computer program instructions to control the imaging module and generate an image based on light emitted from the target region that transmits through the lens module.

16. An imaging assembly comprising:
    a sample platform having a target region;
    an excitation light module arranged proximate to the sample platform;
    a lens module arranged to receive light emitted from the target region, wherein the lens module includes two or more lenses arranged in an uninterrupted series as an optical baffle, the lenses being configured to refract off-normal light toward interior side walls of the lens module;
    a first interference filter, positioned along an optical path in line with and in front of the lens module;
    a second interference filter, positioned along an optical path in line with and behind the lens module;
    an absorbance glass, positioned along the optical path in line with and behind the lens module;
    a light sensor arranged to receive light emitted from the lens module; and an imaging module configured to process data captured by the light sensor.

17. An imaging assembly according to claim 16, wherein the second interference filter and the absorbance glass are physically coupled to each other.

18. An imaging assembly according to claim 16, wherein the second interference filter is positioned in front of the absorbance glass along the optical path.

19. An imaging assembly according to claim 16, wherein the absorbance glass is positioned in front of the second interference filter along the optical path.

20. An imaging assembly according to claim 16, wherein the second interference filter and the absorbance glass have a combined optical density of OD6.

21. An imaging assembly according to claim 20, wherein the interference filter has an optical density of from OD3 to OD4.

22. An imaging assembly according to claim 20, wherein the absorbance glass has an optical density of from OD2 to OD5.

23. An imaging assembly according to claim 16, wherein the excitation light module further comprises an excitation light array that can emit more than one wavelength of light.

24. An imaging assembly according to claim 16, further comprising structural baffles, proximate to the front of the lens module, provided in combination with the optical baffle.

25. An imaging assembly according to claim 16, wherein the sample platform is configured to support a Western blot sample in the target region.

26. An imaging assembly according to claim 16, wherein the excitation light module is arranged in an epi-illumination configuration.

27. An imaging assembly according to claim 16, wherein the absorbance glass is a borosilicate glass.

* * * * *